United States Patent
Wårdell et al.

(10) Patent No.: US 6,300,773 B1
(45) Date of Patent: Oct. 9, 2001

(54) METHOD AND DEVICE FOR TESTING A BRAIN LESION ELECTRODE

(75) Inventors: Karin Wårdell; Ola Eriksson, both of Linköping (SE)

(73) Assignee: Elekta AB, Stockholm (SE)

( * ) Notice: Subject to any disclaimer, the term of this patent is extended or adjusted under 35 U.S.C. 154(b) by 0 days.

(21) Appl. No.: 09/424,529

(22) PCT Filed: Jun. 16, 1998

(86) PCT No.: PCT/SE98/01160

§ 371 Date: Feb. 15, 2000

§ 102(e) Date: Feb. 15, 2000

(87) PCT Pub. No.: WO99/00063

PCT Pub. Date: Jan. 7, 1999

(30) Foreign Application Priority Data

Jun. 26, 1997 (SE) .................................................. 9702462

(51) Int. Cl.[7] .......................... H01H 31/02; G01R 35/00; A61B 19/00; A61B 17/08
(52) U.S. Cl. ........................... 324/555; 606/130; 606/154
(58) Field of Search ................................... 324/555, 607; 606/130, 35; 424/144.1, 133.1, 141.1, 153.1; 607/105, 113, 116, 154

(56) References Cited

U.S. PATENT DOCUMENTS

| | | | |
|---|---|---|---|
| 4,349,909 | * 9/1982 | Cichy | 266/44 |
| 4,409,987 | * 10/1983 | McIntyre | 600/544 |
| 4,411,266 | * 10/1983 | Cosman | 606/49 |
| 4,417,590 | * 11/1983 | Smith et al. | 600/544 |
| 4,488,558 | * 12/1984 | Simbruner et al. | 600/376 |
| 4,638,798 | * 1/1987 | Shelden et al. | 606/130 |
| 4,638,801 | * 1/1987 | Daly et al. | 606/4 |
| 4,651,732 | * 3/1987 | Fredrick | 606/130 |
| 5,116,344 | * 5/1992 | Sundqvist | 606/130 |
| 5,552,713 | 9/1996 | Rashidi | 324/555 |

FOREIGN PATENT DOCUMENTS

| | | |
|---|---|---|
| 3506 186 | 8/1986 | (DE) . |
| 0 416 158 | 3/1991 | (EP) . |

\* cited by examiner

Primary Examiner—Glenn W. Brown
Assistant Examiner—Wasseem H. Hamdan
(74) Attorney, Agent, or Firm—Miles & Stockbridge P.C.

(57) ABSTRACT

A method and a device for testing a brain lesion electrode (1) which is intended for use in treatment of a specified area in the brain, for instance, by controlled coagulation or lessening. The device comprises a transparent container (2) which in adapted to accommodate a solution of coagulatable protein with a predetermined salt content, a seal (6), which the brain lesion electrode (1) can penetrate and which is adapted to seal the container (2) containing the solution, a heating device (3) for heating the solution to a selected temperature, a power unit (23) for supplying, during a selected period, current of a predetermined intensity and frequency between the electrode (1) and a backplate electrode (18) in the container (2) to increase the temperature of the solution in the area at the tip of (21) of the electrode when the electrode (1) is introduced into the solution and positioned therein.

13 Claims, 1 Drawing Sheet

METHOD AND DEVICE FOR TESTING A BRAIN LESION ELECTRODE

BACKGROUND OF THE INVENTION

The present invention relates to a method and a device for testing a brain lesion electrode which is intended for use in treatment of a specified area in the brain, for instance, by controlled coagulation or lessening.

More specifically, the invention relates to a system for quick-testing electrodes that are used in surgical operations in the brain, such as bipolar coagulation and lessening for neurosurgery, and impedance measurement as well as stimulation, at a controlled temperature of the electrode tip.

The brain lesion electrode can be a monopolar electrode, the other electrode or backplate electrode preferably being a metal plate which is arranged in electrically conductive contact with the patient's skin, for instance, on the patient's back. The backplate electrode or reference electrode can also be assembled with the active electrode to form a unit, i.e. a bipolar electrode or a double electrode consisting of two monopolar electrodes.

The above-mentioned electrodes are intended to be used together with a power unit with the possibility of controlling current intensity, frequency, duration of the treatment periods etc. and with monitoring and indicating functions for, inter alia, the temperature of the brain lesion electrode. An example of a suitable power unit is LEKSELL® NEURO GENERATOR, which is commercially available at Elekta Instrument AB in Sweden. A suitable device for positioning and holding the electrode when in use is disclosed in, for example, U.S. Pat. No. 5,116,344.

Before the brain lesion electrode is put into use, it is most important to make sure that the electrode operates in the intended fashion. Of course a built-in test system is available in the power unit, but it may be difficult to discover certain deficiencies of the electrode, such as. a defective thermocouple in the electrode or an unsatisfactory coating of the electrode.

SUMMARY OF THE INVENTION

One object of the present invention therefore is to provide a method and a device for in-situ-testing of the function of the brain lesion electrode.

A further object of the invention is to provide a method and a device which permit a quick, safe and easy test of brain lesion electrodes.

One more object of the invention is to provide an inexpensive and reliable testing device for brain lesion electrodes, which can supplement or be integrated with existing power units as described above.

According to the invention, these objects are achieved by a method, which is characterised by the following steps:

introducing in a transparent container a solution of coagulatable protein with a predetermined salt content conforming with the salt content in a patient's body;

sealing the container with a sealing means, which the brain lesion electrode can penetrate;

heating the solution to a selected temperature in the range 35–40° C.;

introducing the tip of the brain lesion electrode into the container through the sealing means;

supplying, during a selected period, current of a predetermined intensity and frequency between the electrode and a backplate electrode in the container, the temperature of the solution in the area at the tip of the electrode being raised and the solution being locally coagulated; and evaluating the test result by visual inspection of the coagulated area.

A device for use when carrying out the inventive method is characterised in that it comprises a transparent container, which is adapted to accommodate a solution of coagulatable protein with a predetermined salt content, a sealing means which the brain lesion electrode can penetrate and which is adapted to seal the container containing the solution, a heating device for heating the solution to a selected temperature, a power unit for supplying, during a selected period, current of a predetermined intensity and frequency between the electrode and a backplate electrode in the container to increase the temperature of the solution in the area at the tip of the electrode when the electrode is introduced into the solution and positioned therein.

Further developments of the invention appear from the characteristic features stated in the sub claims.

BRIEF DESCRIPTION OF THE DRAWINGS

A Preferred embodiment of the invention will now be illustrated for the purpose of exemplification and with reference to the accompanying drawings, in which.

DESCRIPTION OF PREFERRED EMBODIMENTS

Figure 1:
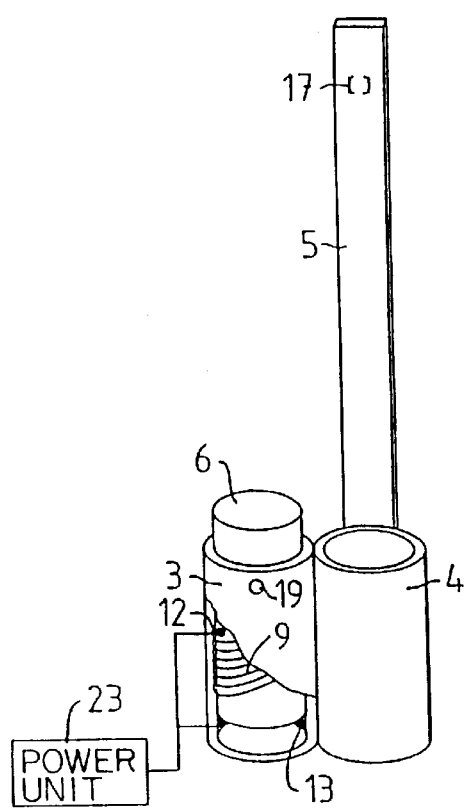
FIG. 1 is a perspective view, partly in section, of the container placed in heating device for heating the test fluid.
Figure 2:
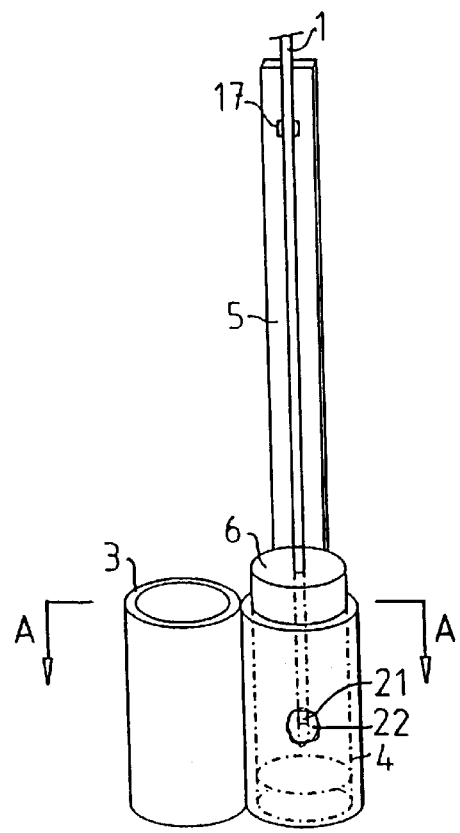
FIG. 2 is a view like the one in FIG. 1 and shows schematically and partly in section the container moved to a holder for carrying out the test according to the invention.

With reference first to FIGS. 1 and 2, a device for testing a brain lesion electrode 1 generally comprises according to the invention a transparent container or vial 2 with a test fluid, a heating device 3 for the container, a holder 4 for holding the container during the tests, a suspension device 5 for fixing the brain lesion electrode 1 during the tests and a power unit which is generally designated 23 and which preferably is a LEKSELL® NEURO GENERATOR.

The test fluid is a solution of coagulatable protein with a salt content which conforms with the salt content in a patient's body to resemble the conditions in the treatment area in the brain. The selected protein is to coagulate at a temperature above 40° C. but below 90° C. A suitable test fluid is an albumin solution. After placing the test fluid in the container 2, this is sealed with a sealing means 6, such as a plug of rubber or foamed plastic, which the brain lesion electrode 1 can penetrate.

Figure 3:
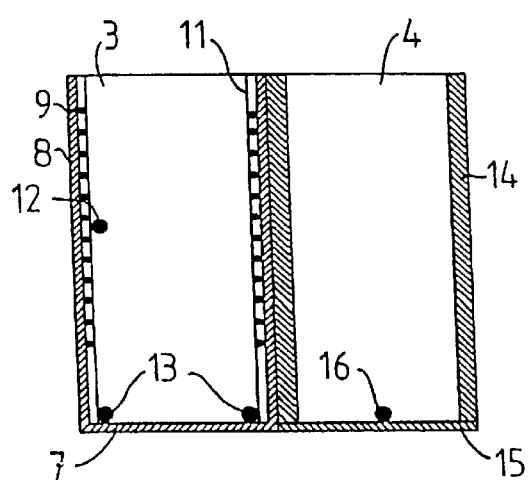
FIG. 3 is a cross-sectional view of the device in FIG. 2 along line A—A, on a larger scale, the container being removed for the sake of clarity.

The heating device 3 can be a device of an optional type, which in a controlled manner can heat the test fluid to a specified temperature selected in the range 35–40° C., preferably 37° C. However, the preferred heating device 3 is a sleeve-like structure with a bottom 7, in the interior of which the container 2 is closely surrounded. In an insulating casing 8 of e.g. plastic material, a heating element is arranged, which comprises a heating wire 9 wound round a drum or tube 11 of metal. A thermistor 12 abuts against the container 2 to register the temperature thereof. Preferably, one or more microswitches 13 are arranged on the bottom 7 of the heating device 3, as schematically shown in FIG. 3, in which case heating can take place only when a container actuates the microswitch 13. The switch 13 thus simplifies the operation of the heating device and is at the same time a safety measure. The heating device 3 can also be equipped with an indicating device 19 which indicates the moment when the container 2 has reached the desired temperature.

In the illustrative embodiment, the indicating device 19 is a light-emitting diode which emits red light during heating and which shifts to green light when the container has reached the set temperature. The above-mentioned electrical components are electrically connected to each other and an external voltage source (not shown), which preferably is to be found in the power unit 23, to which the brain lesion electrode is connected.

Adjacent to the heating device 3, the holder 4 is arranged, which is made of a transparent material to make it possible to visually observe the end or tip 21 of the electrode and the test fluid when the brain lesion electrode 1 has penetrated the sealing means 6 of the container in the holder 4 and current is made to flow from the electrode 1, see FIG. 2. The holder 4 is designed to closely surround the container 2 and consists of a casing 14 with a bottom 15, on which a contact means 16 is arranged, which is electrically connected to said power unit 23.

The suspension device 5 for the brain lesion electrode 1 is preferably fixedly attached to the casing 14 of the holder 4 and comprises a clamping arrangement or snap-on mounting 17 for holding and positioning the electrode during the quick tests, thereby enabling the tip or end 21 of the electrode to be centred in the container 2, see FIG. 1.

Figure 4:
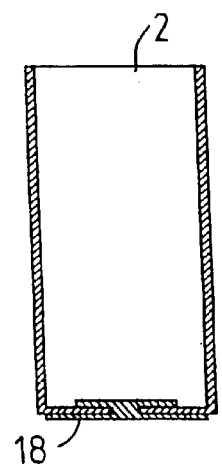
FIG. 4 shows on the same scale as in FIG. 3 a section through the container along its symmetry axis.

The brain lesion electrode 1 cooperates with a backplate electrode or reference electrode, current flowing between the electrodes. The backplate electrode and the brain lesion electrode can be formed as a unit, i.e. a bipolar electrode or a double electrode consisting of two monopolar electrodes, as is previously known. In the above-mentioned case, the contact means 16 is not necessary since current flows from one electrode to the other in the unit via the saline test fluid. However, for testing a monopolar brain lesion electrode, the contact means 16 is necessary, as is also a specially designed container 2. With reference to FIG. 4 a container 2 is shown which is intended for use together with a monopolar brain lesion electrode 1. Since the container is made of an electrically non-conductive material, such as glass, the backplate electrode is designed as a separate unit 18, which is preferably arranged on the bottom of the container in conductive communication with the inside as well as the outside of the container. FIG. 4 illustrates this in such a manner that the backplate electrode 18 comprises an inner plate and an outer plate, which are interconnected by means of a portion extending through the bottom of the container. The backplate electrode is connected with the bottom in a fluid-tight manner with the aid of some suitable means. When the container with the test fluid is immersed in the holder 4, the backplate electrode 18 is electrically contacted with the contact means 16, and current can flow from the electrode 1, through the test fluid and via the backplate electrode 18 back to the power unit 23.

The method according to the invention for testing a brain lesion electrode is evident from the above description, but a summary may be convenient.

A solution of coagulatable protein with a predetermined salt content (for instance 15 ml albumin solution) is inserted into a transparent container or vial 2, which is sealed with a penetratable sealing means 6. Then the container 2 is inserted into the heating device 3, which preferably is electrically connected to the power unit 23. The microswitch 13 is switched on by the container 2 and current flows through the heating wire 9, the generated heat being distributed over the drum 11 and being uniformly transmitted to the container and to the test fluid. The light-emitting diode 19 emits red light and the heating begins. When the thermistor 12 registers that the selected temperature has been reached, the light-emitting diode changes colour and the container is ready to be (manually) moved to the holder 4.

When the container 2 has been inserted into the holder 4, the tip 21 of the brain lesion electrode 1 is made to penetrate the sealing means 6, the electrode tip 21 is positioned approximately in the centre of the container 2, and the brain lesion electrode is fixed by means of the clamping arrangement 17 of the suspension device 5. During one or more selected periods, the power unit 23 then makes current of a predetermined intensity and frequency flow between the brain lesion electrode 1 and the backplate electrode 18 through the test fluid, the temperature in the fluid in the area at the tip 21 of the brain lesion electrode being increased and the fluid being locally coagulated, as indicated by reference numeral 22. A usually preferred heating temperature is about 70° C. and a frequency is about 0.5 MHz.

By visually inspecting the coagulated area 22, it is possible to discover deficiencies of the electrode or its function and also to obtain an indication of the result of a specific setting of certain parameters in the power unit 23.

After completion of the test, the brain lesion electrode is removed, and the container with the test fluid can be reused or rejected, as required.

The invention is not limited to that described above or shown in the drawings, and can be modified within the scope of the appended claims.

What is claimed is:

1. A method for testing a brain lesion electrode which is intended for use in treatment of a specified area in the brain, by controlled coagulation or lesioning, characterised by the following steps:
   a. introducing in a transparent container a solution of coagulatable protein with a predetermined salt content conforming with the salt content in a patient's body;
   b. sealing the container with a seal, which the brain lesion electrode can penetrate;
   c. heating the solution to a selected temperature in the range 35–40° C.;
   d. introducing a tip of the brain lesion electrode into the container through the seal;
   e. supplying, during a selected period, current of a predetermined intensity and frequency between the brain lesion electrode and a backplate electrode in the container, the temperature of the solution in the area of the tip of the brain lesion electrode being raised and the solution being coagulated in a local area; and
   f. evaluating a test result by visual inspection of the coagulated local area.

2. a method as claimed in claim 1, characterised by heating the container in step c in a separate heating device surrounding the container, and moving the container, when the solution has reached the selected temperature, to a transparent holder enclosing the container.

3. a method as claimed in claim 1, characterised by fixing the brain lesion electrode in step d relative to the interior of the container by means of a suspension device.

4. a device for testing a brain lesion electrode, characterised in that it comprises a transparent container, which is adapted to accommodate a solution of coagulatable protein with a predetermined salt content, a seal which the brain lesion electrode can penetrate and which is adapted to seal the container containing the solution, a heating device operative to heat the solution to a selected temperature, a power unit operative to supply, during a selected period, current of a predetermined intensity and frequency between the brain lesion electrode and a backplate electrode in the container to increase the temperature of the solution in the area at a tip of the brain lesion electrode when the brain lesion electrode is introduced into the solution and positioned therein.

5. a device as claimed in claim 4, characterised in that the heating device is constructed to receive and surround the container and adapted to break off the heating of the solution when the solution has reached the selected temperature, and further comprising a transparent holder constructed to receive and surround the container during testing.

6. a device as claimed in claim 5, characterised in that the heating device comprises a heat-insulating casing, a heating wire wound round a metal drum, which is adapted to closely surround the container, a thermistor arranged to abut against the container to sense the temperature thereof, and a microswitch in the bottom of the heating device and operative to activate the heating device when the container is inserted into the heating device.

7. a device as claimed in claim 6, characterised in that the thermistor is connected to an indicating device indicating the moment when the solution has reached the selected temperature.

8. A device as claimed in claim 6, characterised in that the backplate electrode is a separate unit, which is arranged on the bottom of the container and extends from the inside to the outside of the container, and that an electric contact is arranged on the inside of the holder for electric contact with the backplate electrode, thereby enabling the backplate electrode to be electrically connected with the power unit.

9. A device as claimed in claim 6, characterised by a suspension device, which is arranged adjacent to the holder and by which the brain lesion electrode can be fixed in position with its tip positioned inside the container.

10. a device as claimed in claim 5, characterised in that the backplate electrode is a separate unit, which is arranged on the bottom of the container and extends from the inside to the outside of the container, and that an electric contact is arranged on the inside of the holder for electric contact with the backplate electrode, thereby enabling the backplate electrode to be electrically connected with the power unit.

11. A device as claimed in claim 10, characterised by a suspension device, which is arranged adjacent to the holder and by which the brain lesion electrode can be fixed in position with its tip positioned inside the container.

12. a device as claimed in claim 5, characterised by a suspension device, which is arranged adjacent to the holder and by which the brain lesion electrode can be fixed in position with its tip positioned inside the container.

13. a device as claimed in claim 4, characterized in that the backplate electrode and the brain lesion electrode are formed as a unit.

* * * * *